United States Patent
Dvorsky

(10) Patent No.: US 7,755,488 B2
(45) Date of Patent: Jul. 13, 2010

(54) ACCESS DISCONNECTION DETECTION SYSTEM

(75) Inventor: James E. Dvorsky, Norwich Township, OH (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 293 days.

(21) Appl. No.: 11/859,419

(22) Filed: Sep. 21, 2007

(65) Prior Publication Data
US 2009/0079578 A1 Mar. 26, 2009

(51) Int. Cl.
*G08B 13/14* (2006.01)
(52) U.S. Cl. ............... 340/572.1; 340/573.5; 600/302
(58) Field of Classification Search ............. 340/573.1, 340/573.4, 573.5, 572.1, 572.4, 539.11; 600/302, 600/485, 486, 509, 513; 705/3
See application file for complete search history.

(56) References Cited

U.S. PATENT DOCUMENTS

| | | | |
|---|---|---|---|
| 4,510,489 | A | 4/1985 | Anderson, III et al. |
| 5,427,695 | A | 6/1995 | Brown |
| 6,069,564 | A | 5/2000 | Hatano et al. |
| 6,071,421 | A | 6/2000 | Brown |
| 6,154,137 | A | 11/2000 | Goff et al. |
| 6,509,217 | B1 | 1/2003 | Reddy |
| 6,897,809 | B2 | 5/2005 | Carson et al. |
| 7,050,047 | B2 | 5/2006 | Hong |
| 7,052,480 | B2 | 5/2006 | Han et al. |
| 7,059,518 | B2 | 6/2006 | Forster |
| 7,102,572 | B2 | 9/2006 | Okado |
| 7,170,414 | B2 | 1/2007 | Clifford et al. |
| 7,416,530 | B2 * | 8/2008 | Turner et al. ................. 600/485 |
| 2002/0145525 | A1 | 10/2002 | Friedman et al. |
| 2003/0199778 | A1 | 10/2003 | Mickle et al. |
| 2004/0113801 | A1 | 6/2004 | Gustafson et al. |
| 2004/0212504 | A1 | 10/2004 | Forcier et al. |
| 2006/0097920 | A1 | 5/2006 | Lin et al. |

(Continued)

FOREIGN PATENT DOCUMENTS

WO 2006/086423 A2 8/2006

(Continued)

OTHER PUBLICATIONS

Puckett, L.B. et al, Monitoring Blood Coagulation With Magnetoelastic Sensors, Biosensors and Bioelectronics, 2003, pp. 675-681, vol. 18 (2003), Elsevier Science B.V.

*Primary Examiner*—Van T. Trieu
(74) *Attorney, Agent, or Firm*—K&L Gates LLP

(57) ABSTRACT

An access site disconnection system and method employ RFID sensors that are sensitive to moisture and their presence may not be detected if the sensor is wetted. When a patient receives dialysis treatment, wetness may arise from blood if the access needle becomes disconnected from the access site. At least one RFID sensor is mounted on or near gauze or other absorbent material placed adjacent the access site. After the sensors are placed, the dialysis machine and RFID control circuit may be initialized and dialysis treatment, such as hemodialysis, begun. If blood leaks from the access site, such as if the access needle is dislodged, the RFID sensor is wetted and sends a different or no response to periodic inquiries from an RFID reader. A signal is sent to a controller or to an output device to raise an alert or sound an alarm.

22 Claims, 8 Drawing Sheets

U.S. PATENT DOCUMENTS

| | | |
|---|---|---|
| 2006/0130591 A1 | 6/2006 | Perkins |
| 2006/0289640 A1 | 12/2006 | Mercure et al. |
| 2007/0096919 A1 | 5/2007 | Knadle, Jr. et al. |
| 2007/0100666 A1* | 5/2007 | Stivoric et al. ................. 705/3 |
| 2008/0150732 A1* | 6/2008 | Bunza et al. ............. 340/573.5 |
| 2008/0306359 A1* | 12/2008 | Zdeblick et al. ............. 600/302 |

FOREIGN PATENT DOCUMENTS

| | | |
|---|---|---|
| WO | 2007/069968 A1 | 6/2007 |
| WO | PCT/US2008/066062 | 9/2008 |

* cited by examiner

ACCESS DISCONNECTION DETECTION SYSTEM

BACKGROUND

The field of the invention is medical treatments generally and patient vascular access systems. The present invention relates to embodiments of a method and a system for detecting disconnection of an access needle or catheter while receiving medical treatment.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from a number of complications that can arise from continuing therapeutic procedures, and even from diagnostic procedures, that are necessary for their continued care. Treatments involving extracorporeal blood treatment are clear examples.

The most obvious danger is infection, but the harm caused by infection can be overcome by not re-using even supposedly-sterile devices, by diligent attention by the patient himself or herself, and by the careful attention of care givers attending the patient. Other problems also arise, but, like infections, have been difficult to eradicate. One of the problems arises in blood treatment procedures in which the patient's blood is physically removed for treatment and then returned, all in the same procedure. Removal and return of blood is practiced in hemodialysis, for those persons whose kidneys do not function well. Other procedures, such as apheresis, involve removing blood from a patient or a donor, subjecting the blood to a centrifugal treatment to separate blood platelets or plasma from red blood cells, and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. A batch treatment is typically short, and the treatment is attended by a medical professional at a clinic or hospital. Other treatments are continuous, such as the platelet separation discussed above, or dialysis treatment, and may require a duration of several hours or even overnight. There is also a "batch continuous" method in which a single needle is used. There are distinct draw and return phases of a batch continuous process. During the draw phase, blood is processed and additional blood is sent to a holding container to be processed during the return phase. During the return phase, blood is processed from the holding container and returned to the patient/donor through the single needle.

Continuous treatments thus require two needles, or access points, one for withdrawal of blood and one for return. The withdrawal site is normally an artery although a vein could also be used, and a needle and a pump are used to provide the blood to the therapeutic machine. It is relatively simple to detect a problem with withdrawal, for instance, if the withdrawal needle is dislodged. Bubbles form in the withdrawal line and conventional air sensors detect the bubbles. Detecting a problem in the return of the blood to the patient is more difficult. The return line is typically a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. The photosensor could also fail to detect light because the needle has not been dislodged sufficiently to expose the photosensor to light.

Another example is U.S. Pat. No. 7,052,480, in which an induction coil is attached to a venous blood line and a second coil is attached to the arterial blood line. An electric current is generated and injected into the blood circuit, passing from one coil through the blood to the second coil. Signal processing circuitry is able to detect any variation in the resulting current in the second coil, and can interpret any significant change in the current, impedance, voltage, resistance, and so forth, as an indication of a leak or of dislodgement. This technique is complicated and difficult to set up for consistent, reliable operation, in consideration of natural variances over long periods of time, and also considering differences between patients.

Another example is provided in U.S. Pat. No. 7,060,047, in which an electric signal is also injected into the patient and is used to form a capacitor. A ring electrode is placed around the tubing of the venous branch, between the drip chamber of a hemodialysis machine and the access needle returning blood to the patient. The blood of the patient forms the other plate of the capacitor. An electronic circuit is used to monitor the voltage across the plates of the capacitor. When the venous access needle is dislodged, a large change in the voltage results, and is detected by the electronic circuit. This technique has the disadvantage that a voltage change may not result until the blood has been exhausted and no longer fills the tubing in the return line.

Numerous other techniques have been devised, many of them depending on a flow of blood causing conductivity between two electrodes or two wires. One problem with these methods is that it is not easy to distinguish between small amounts of blood and the natural perspiration of a person, which can cause false alarms. What is needed is a better way of quickly detecting dislodgement of a venous or other needle or catheter from a patient, so that inadvertent loss of blood and harm to the patient is avoided.

Another drawback to many of these detection methods is the need to establish another patient connection to or from the therapeutic equipment. For example, in U.S. Pat. Appl. Publ. 2006/0130591, an electrical connection between the hemodialysis machine, or other monitor of access disconnection, and the photosensor must also be established between the patient and the hardware. Ideally, only the arterial and venous access lines necessary for continuous therapy are between the patient and therapeutic equipment, while still providing a means of ensuring patient safety in the event of a venous access disconnection

SUMMARY

One embodiment is an access disconnect detector. The access disconnect detector includes at least one RFID sensor, and a mount suitable for mounting the at least one RFID sensor, wherein the mount and the at least one RFID sensor are configured for positioning adjacent a dialysis access site for detecting a presence of blood of a patient, and wherein the at least one RFID sensor is configured for communication with an RFID reader so that the RFID reader receives one response from the sensor when the sensor is dry and receives a different response or no response when the sensor is wetted with blood.

Another embodiment is an access disconnect detector. The access disconnect detector include a flexible mount suitable for attaching to a patient, at least one RFID sensor mounted on the mount, and a pad of absorbent material on an opposite side of the at least one sensor, wherein the mount and the at least one RFID sensor are configured for positioning adjacent an access site for detecting a presence of blood of the patient, and wherein the at least one RFID sensor and an RFID reader are configured so that the RFID reader receives one response when the at least one sensor when the at least one sensor is dry and receives a different response or no response from the at least one sensor when the at least one of the sensors is wetted with blood.

Another embodiment is an access disconnect detector. The access disconnect detector includes a plurality of RFID sensors for placement in a pattern on a person and a flexible, porous layer adjacent the RFID sensors, wherein the RFID sensors and the pattern are configured for rapid detection of blood from the person. Another embodiment is a method for detecting an access site disconnection. The method includes steps of placing an RFID detector including at least one RFID sensor on or adjacent the access site, detecting the at least one RFID sensor with an RFID reader by pulsing and noting a response from the at least one RFID sensor, periodically repeating the step of detecting, and sending a signal if the step of detecting receives a different response or no response from the at least one RFID sensor.

Additional features and advantages are described herein, and will be apparent from, the following Detailed Description and the figures.

DETAILED DESCRIPTION

Figure 1:
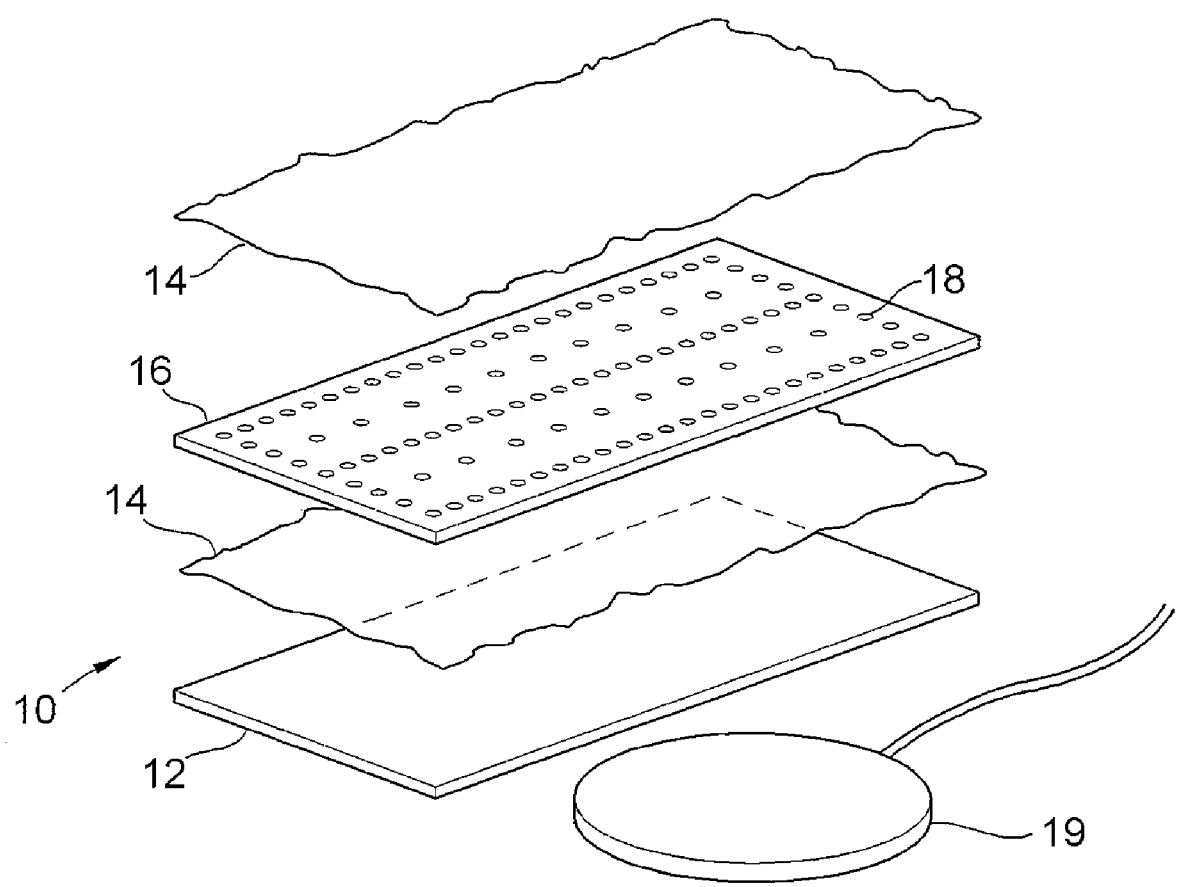
FIG. 1 is a perspective view of a first embodiment of an RFID sensor useful in an access disconnect detection system.

As noted above, one difficulty with extracorporeal blood treatment systems is the possibility that the needle or catheter providing vascular access could be accidentally removed or become dislodged. Depending on the flow rate of the blood, if the venous access or return is dislodged, a great loss could occur in a very short time. Accordingly, an access disconnect detection system has been invented to detect removal or dislodgement of a needle or catheter, or leaking of blood, during hemodialysis treatment. Of course, the access disconnect detection systems described herein can be used for many other types of medical treatment, and are most useful for those that involve extracorporeal treatment of a patient's blood. Besides hemodialysis, these treatments include centrifugal separation of blood platelets or plasma from the blood, and then returning the red blood cells to the patient or donor.

The sensors described herein are intended as passive sensors, that is, they do not have a battery or other power source except for the RFID reader or other interrogation source. Sensors or tags with a power source, generally known as active sensors, may also be used, but in general they cost more and may offer only marginal advantages in the uses described herein. In this patent, the term RFID tags is used merely to distinguish the sensors herein described from commercially available RFID tags, such as those used to identify products or for electronic article surveillance. In general the term radio-frequency is intended to designate frequencies from about 50 kHz to 2.45 GHz. Higher or lower frequencies may also be used, but at present equipment for higher or lower frequencies is not commercially available.

Strictly speaking, embodiments of the invention are not using radio-frequency identification, since unique identification may not be involved. Rather, the embodiments are simply using radio-frequency pulses to determine whether the functionality of one or more of a particular set of radio-frequency circuits on a patient have been changed. If one or more of the sensors associated with a patient has been changed or damped, in general it does not matter which one, and thus identification may not be needed or used. In addition, the circuits described herein are very low power, which helps to minimize the chance of confusing the sensor used for one person or patient with another. Nevertheless, it may be useful to retain an ability to identify each particular sensor, and the term RFID is easier to use than "radio-frequency" in describing a circuit or an object and thus is used herein, whether or not identification is possible or is desired.

An RFID sensor herein is an RFID circuit whose operation is changed or damped when wetted with blood. As will be described herein, the damping may be intrinsic, as when blood infiltrates the circuit and causes a physical change in a vibrating part, typically in circuits using a lower frequency radio-frequency pulsed inquiry. The damping may instead be caused by scattering or absorption of the inquiring signal, which typically happens when a higher frequency radio-frequency pulsed inquiry encounters water or blood adjacent the RF circuit. This results in very little signal reaching the RFID tag or sensor, with no return signal.

A first embodiment of an access disconnect detection sensor is depicted in FIG. 1. In this embodiment, the sensor 10 includes a pad 12, a first layer of absorbent material 14, such as gauze, an RF-responsive metallic layer 16, and a second layer 14 of absorbent material. It is intended that the first layer 14 is adjacent the patient, that is, adjacent the access site. The RF-responsive metallic layer 16 is placed next, the metallic layer including a plurality of orifices 18 to encourage wicking of blood into the orifices. A second layer 14 of absorbent material, such as gauze, overlies the other side of the metal layer 16. The layers may be assembled by sewing or other technique. Adhesives on the RF-responsive metallic layer may tend to damp the layer prematurely.

The materials useful for the sensor 10 include first a gauze, or other absorbent material. Gauze, for example, the sort of gauze used for bandages, does not irritate the patient's skin, is readily available, and absorbs blood. A similar material is cheesecloth. The absorbent material should absorb blood, rather than to repel it, and thus may be treated with a hydrophilic agent, such as a hydrophilic surfactant. If the catheter or needle is dislodged, blood will flow outside the needle, to the patient's detriment. The sensor should detect the presence of blood as soon as possible. Thus, the gauze will wick blood and pass the blood through to the next layer.

Mounting layer 12 should be firm enough so that it is easy to handle by a caregiver, such as a nurse or an aide, and yet should be flexible, so that it conforms to the patient's shape, for example, when it is draped across an arm of the patient. Layer 12 may be a thin plastic or elastomeric layer about 1-2 mm thick, although thicker or thinner layers will also suffice. It may be porous, for example, a foamed material, or may be solid, and should be sterile, as the absorbent layers should be sterile, to avoid any possibility of infection for the patient. It should also be capable of mounting RFID sensors on one side, as discussed below, and an RFID reader on the opposite side. Examples of materials that may be used include silicone or urethane elastomers and polyethylene and polypropylene plastics.

The metallic layer 16 of the RFID sensor 10 is any metal that is responsive to radio-frequency excitation. Examples include strips of magnetoelastic metals, magnetoacoustic metals, magnetostrictive amorphous metal alloys, and amorphous metal alloys. Some of these materials are disclosed in U.S. Pat. No. 4,510,489, which is hereby incorporated by reference in its entirety. An example of such amorphous metals is given by the formula $M_a N_b O_c X_d Y_e Z_f$, where M is at least one of iron and cobalt, N is nickel, O is at least one of chromium and molybdenum, X is at least one of boron and phosphorus, Y is silicon, and Z is carbon. The subscripts, a-f, are in atomic percent, and a ranges from about 35-85, b from about 0-45, c from about 0-7, d from about 5-22, e from about 0-15, and f ranges from about 0-2, and the sum of d+e+f ranges from about 15-25. These alloys typically require heat treating to achieve the desired properties.

Amorphous metals are available from MetGlas®, Inc., Conway, S.C., U.S.A. and from Siemens AG, Munich, Germany. Other metals with desirable magnetic properties useful in these application, such as Hy-Mu "80"® alloy are available from Carpenter Technology, Reading, Pa., U.S.A. These materials are more useful at lower frequencies, such as 58-125 kHz. Other, similar materials may be obtained from a variety of other sources.

Without being bound to any particular theory, sensors made with these metals are believed to behave in the manner herein described. An RFID transmitter/receiver, also known as an RFID reader, sends a signal by emitting an electromagnetic wave. A radio-frequency sensor or RFID tag nearby receives the wave and itself begins to vibrate. This results in another electromagnetic wave having a frequency at or near the mechanical resonant frequency of the sensor, which is then detected by the RFID reader. The metal strips described above are believed to work best at relatively low frequencies, from about 50-150 kHz. One of their properties at these low frequencies is that moisture minimally interferes with the RF signal. At higher operating frequencies, such as 13.56 MHz and 915 MHz, the performance of an RFID sensor on or within an electrically-conducting object, such as a metallic beverage container, is compromised. The conducting material in proximity to the sensor scatters the signal and interferes with operation of the RFID sensor. Thus, absorption of body fluids in gauze or other material in contact with RFID sensors operating at higher frequencies will result in no interrogation signal reaching the sensor or no return signal emanating from the sensor, or both, and will be interpreted as detection of liquid or blood.

Figure 2:
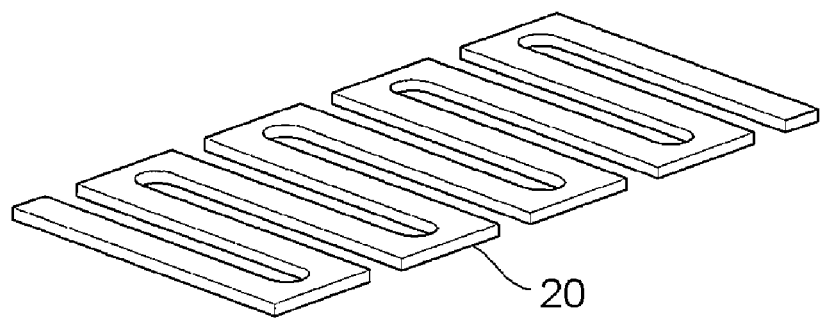
FIGS. 2-3 are perspective views of alternate materials useful in the embodiment of FIG. 1.

At lower frequencies, however, such as those useful for the metal strips discussed above, the presence of blood will mechanically dampen the vibrations induced in the sensor and thus diminish the return signal delivered to the RFID reader. Accordingly, the metal strips are configured with orifices 18, as depicted in FIG. 1, or with a serpentine pattern 20, as shown in FIG. 2. If the catheter or needle at the access site becomes disconnected, blood with flow into the gauze and be wicked from the gauze into the thin metal strip. The orifices 18 or serpentine paths 20 cut into the metal will quickly be filled with blood, a viscous material, via capillary action. The blood will dampen the vibrations of the metal in response to the interrogating pulse from the reader, and the reader will receive no response, or a different or significantly reduced response. The reader may be programmed to interpret such responses as a disconnect or possible disconnect, and will send a signal or raise an alert to the user, to a care giver, or to a medical professional administering the therapy.

Fluid viscosity is known as one of the physical parameters that can be measured by sensing devices, such as RFID sensors. Grimes, et al have shown that a variety of physical parameters may be measured by sensing devices such as those described herein, when the sensing element is in the medium whose parameter(s) is to be measured. One of these parameters is fluid viscosity, and by detecting variations in response frequency from the vibrating element, the viscosity of fluid surrounding the element can be measured. Since the viscosity of human blood is two to three times higher than water, the detection system described in this patent is further refined to distinguish blood from water or perspiration. See *Wireless Magnetoelastic Resonance Sensors: A Critical Review,* Craig A. Grimes et al., Sensors, Vol. 2, pp. 294-313 (2002). Because of the higher viscosity of blood, the mechanical loading on the vibrating element will be larger than that expected from water or perspiration. Therefore, the response at low frequency will be more highly damped when the sensor is wetted with blood than with water or perspiration. At high frequency, the viscosity of the blood is not expected to affect the response of the sensor as much as at low frequency.

Figure 3:
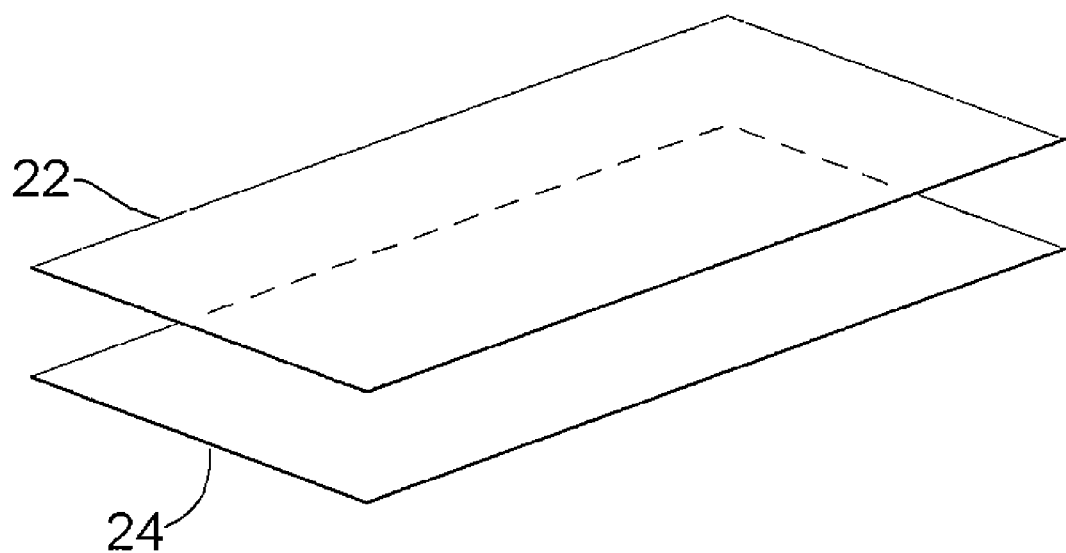
Figure 4:
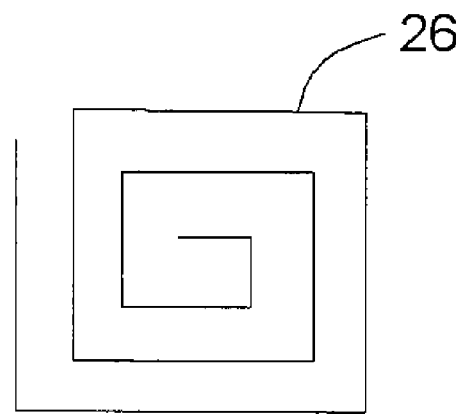
FIGS. 4-7 are embodiments of antennae useful in RFID sensor.
Figure 5:
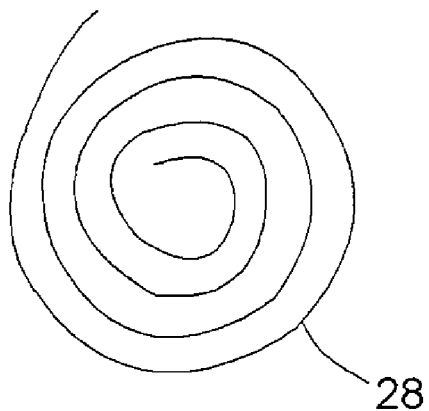
Figure 6:
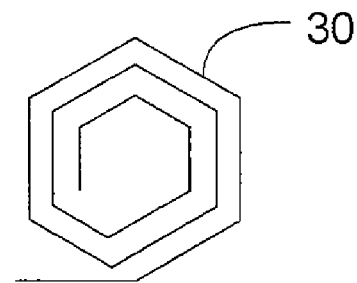
Figure 7:
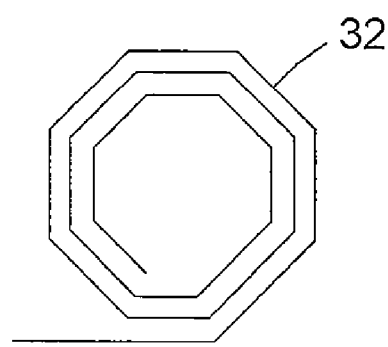

In one embodiment, the strips of interest will be about 3 cm long by about 0.5 cm wide, and about 0.2 mm thick. The orifices 18 in FIG. 1 may be about 0.5 mm in diameter. The paths in the serpentine configuration 20 in FIG. 2 may be about 0.5 mm wide. In another embodiment, as shown in FIG. 3, the detector may use strip 22 and a magnetized ferromagnetic element 24 of about the same size and shape. As also described in U.S. Pat. No. 4,510,489, the magnetized ferromagnetic element is placed adjacent a ductile magnetostrictive ferromagnetic strip. The magnetized ferromagnetic element may be, for example SAE 1095 (AMS 5121F, wrought carbon steel), or other metal of high coercivity. Typically, the strips are placed into a rigid container, such as a plastic container, to ensure their continued performance. In this application, they are placed into a container which will restrain their edges and hold their shape, but which allow blood to infiltrate and dampen the vibrations resulting from pulses from the reader. In another embodiment, a single strip 22 of metal as discussed above, may be used instead, as shown in FIGS. 1-2.

In use, it is contemplated that an RFID sensor 10, such as one depicted in FIG. 1, will be placed on an access site, the first absorbent or gauze layer adjacent the access site. The sensor 10 may be taped onto the patient, such as by one or more of its outer edges. An RFID reader 19 is placed on the bottom side of pad 12, which in this figure, faces away from the patient. The RFID reader 19 should clearly be small, not more than a few square cm of surface area, for ease of placement and comfort to the patient for a procedure that may last several hours or even overnight. In other embodiments, one or more smaller RFID sensors 10 will be positioned on the pad and near the access site, so that their vibration response changes quickly if the needle is dislodged or when blood leaks for any other reason. In other embodiments, the RFID reader 19 will be on or adjacent the hemodialysis or other therapy machine. This avoids the need for any further connections to the patient.

In order to detect blood leakage and any disconnect as soon as possible, the RFID reader 19 will pulse the sensors periodically, at a rate from about twice per second to about once every 2 seconds, e.g., from about 0.5 to about 2 Hz. In order to minimize false alarms, the RFID reader 19 may be programmed to continue pulses without sending an alert or alarm signal until more than one no-response or modified response is detected, that is, only sending an alert or alarm signal after a given number of no-responses or modified responses, such as 2, 3, or 5 failures to respond or modified responses. The number selected will help avoid false positives without unduly delaying the alert or causing significant additional blood loss.

The RFID sensors 10 described above operate on the principle that their vibratory responses change upon contact with blood. Other passive RFID sensors 10 work in this application by scattering the inquiring RFID pulse and failing to vibrate, and thus failing to send back a signal to the reader. These RFID sensors 10 typically operate at higher commercial frequencies, from about 5-7 MHz to 13.56 MHz, 860-960 MHz (generally termed 915 MHz) and up to 2.45 GHz. The problem of interference by water or other liquid in these higher frequencies is overcome by providing a gap between the metal surface and the RFID circuit. This is why some of the small RFID tags used commercially for electronic article surveillance (EAS) are so thick, several mm thick, when a printed inlay type RFID tag would suffice. Embodiments described herein take advantage of this effect by placing RFID sensors 10 adjacent the patient with minimal gap or offset, such as the absorbent layer, so that the inquiring RFID signal will be scattered and blood detected as soon as blood appears. Thus, when the sensor 10 is wetted with blood, it will emit no response or a changed response to an inquiry by an RFID reader.

These higher-frequency RFID sensors 10 typically include an antenna and a small integrated circuit (IC) in electrical contact with the antenna. The integrated circuit or "chip" contains programmed information and may be interrogated for that information. Thus, the IC may be programmed with information about its association with a product, a manufacturer, a lot number and so forth. In the present application of RFID sensors 10, however, this information, while useful, may not be essential. All that is really needed is for an antenna to receive a signal from an RFID reader 19 and to generate a sympathetic vibration or electronic response in return that is detected by the RFID reader 19 when the antenna is dry. The antenna should not generate the same vibration or electronic response when the sensor is wetted with blood. Of course, the sensor 10 or sensors may be programmed with information about the hospital or clinic, about the patient, the patient's medical history, the previous treatment, and so forth. For these reasons, an antenna may continue to be teamed with a chip to provide the identification portion of RFID.

Figure 8:
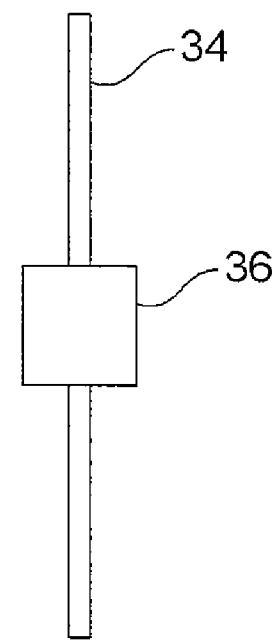
FIGS. 8-11 are RFID circuits useful in RFID sensors.
Figure 9:
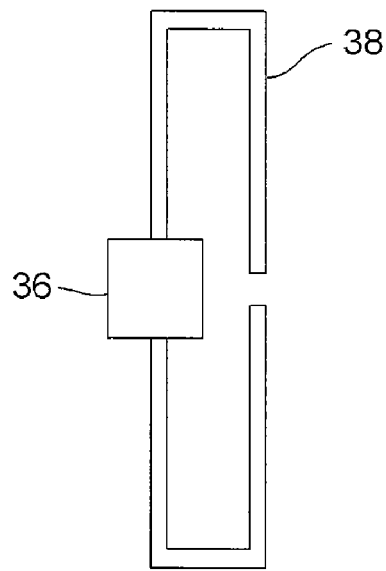

Antennae may be made in many configurations, as shown in the planar spiral configurations of FIGS. 4-7, with square planar antenna 26, circular planar antenna 28, hexagonal planar antenna 30, and octagonal planar antenna 32. Dipole antennae, such as those of FIGS. 8-9, may also be used. In FIG. 8, the antenna 34 includes two dipoles in contact with an integrated circuit 36 to form an RFID tag or sensor useful in embodiments. In FIG. 9, a more complicated dipole 38 is also joined to an integrated circuit 36.

Figure 10:
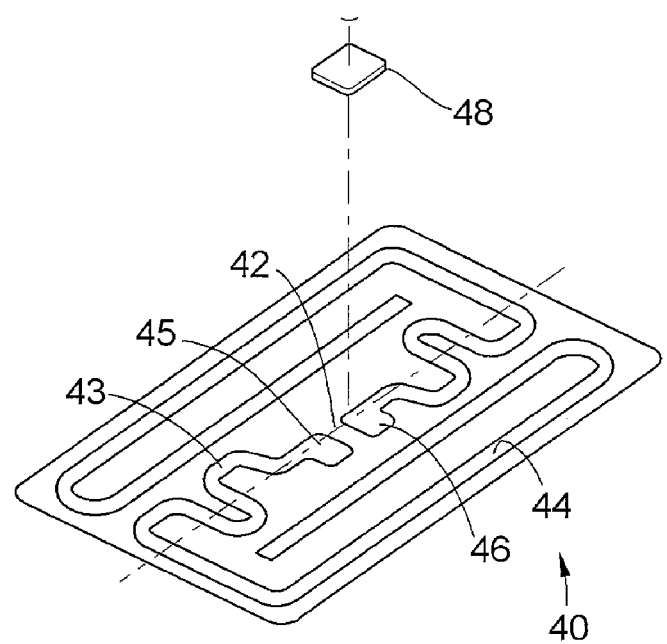
Figure 11:
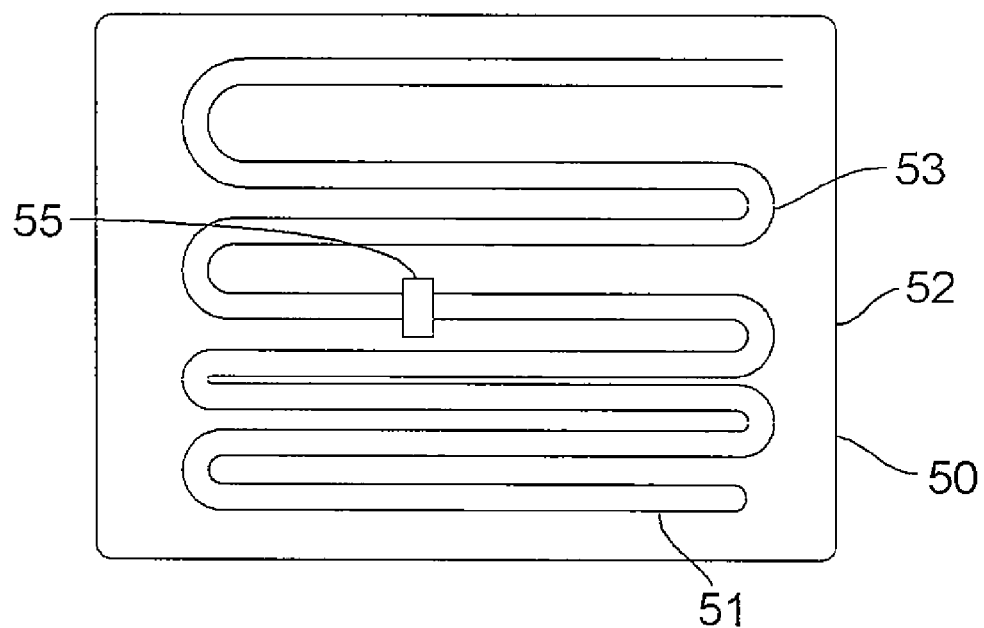

Many of these metallic antennae may be printed, as on paper or film substrates, as shown in FIG. 10, with subsequent connection to a chip. One example is ink jet printing. RFID tag or sensor 40 includes a paper substrate 42, a printed first antenna 43 with a pad 45 and a second printed antenna 44 with a pad 46. Integrated circuit or chip 48 is placed on the substrate and connected by any suitable technique, for example, by using pads made from conductive material or adhesive. The antennae and pads are made from a conductive ink or coating that is printed onto the substrate. Another example of a simple RFID sensor is depicted in FIG. 11. RFID sensor 50 includes a substrate 52, printed antennae 51, 53, and a chip 55. The chips are available from many sources, such as Microchip Technology Inc., Chandler, Ariz., U.S.A.

Figure 12:
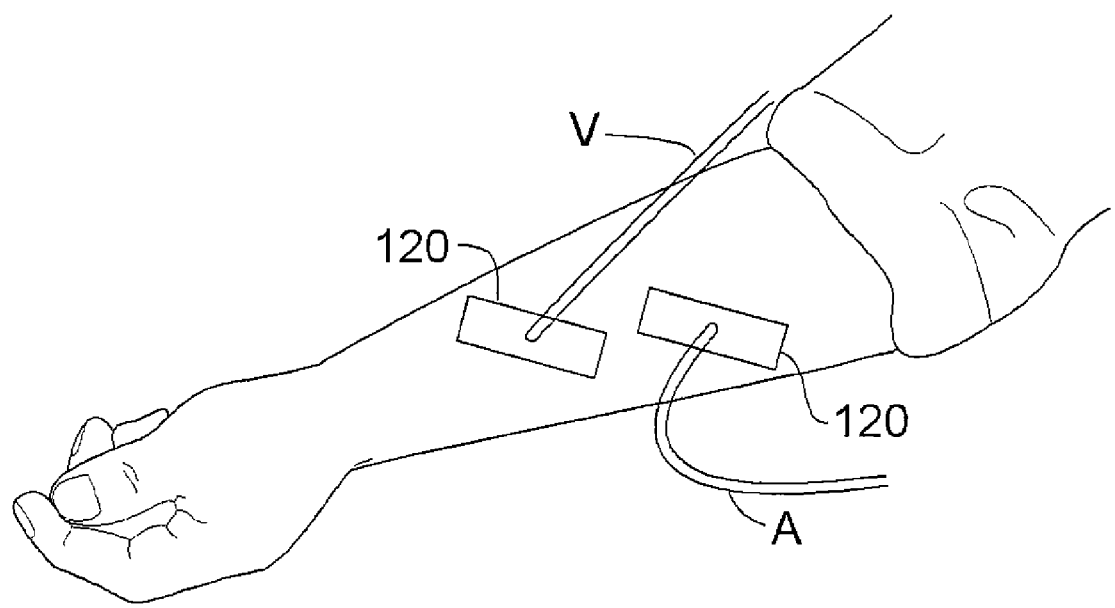
FIG. 12 depicts use of an access disconnect detector.
Figure 13:
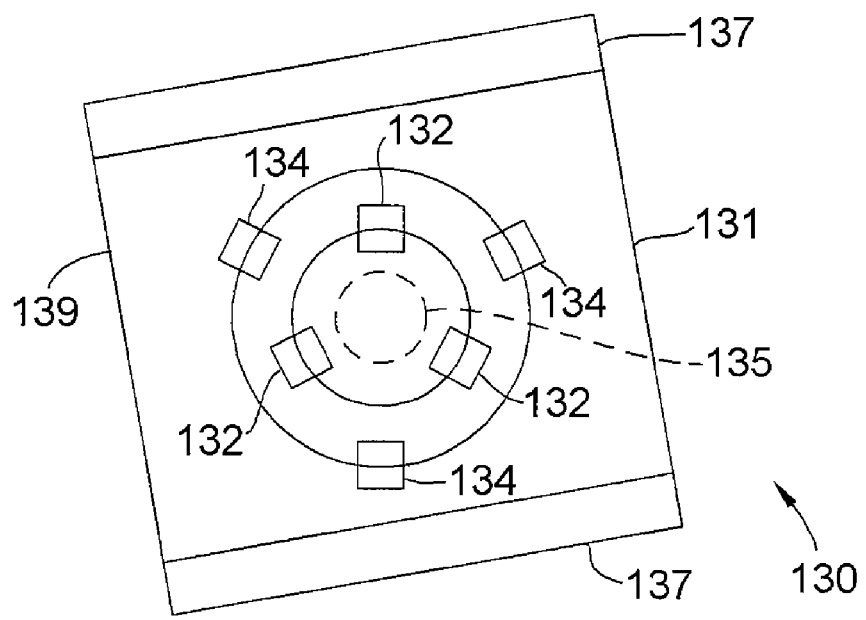
FIGS. 13-14 depict sensor arrays useful in an access disconnect detector.
Figure 14:
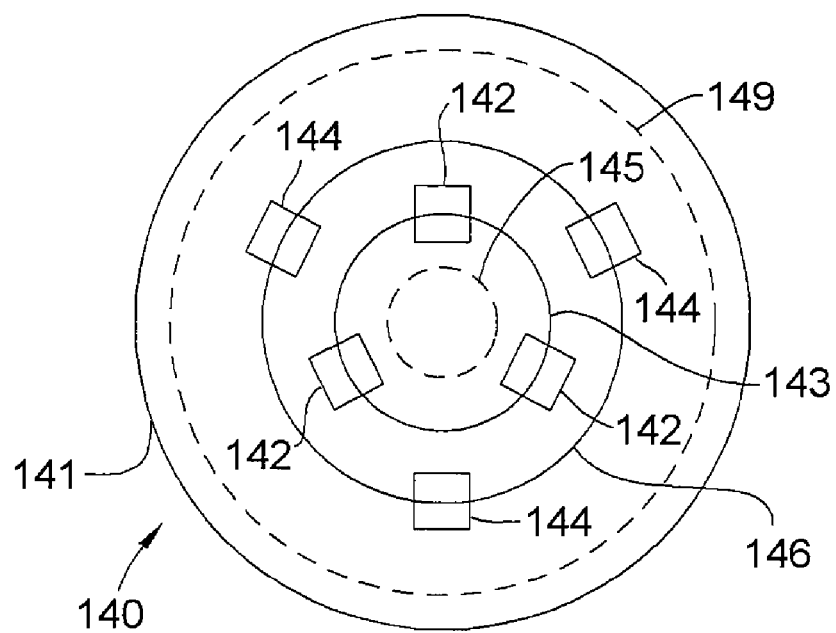

To use the access disconnect sensor, the sensor or sensors 120 are placed over access sites on a patient P, as shown in FIG. 12. Patient P has two access sites, one A for arterial access, sending blood to a hemodialysis machine, for example, and a second V for venous access, for returning the blood to the patient. Sensors 120 are placed over the access sites, as shown. Examples of suitable sensors are depicted in FIGS. 13-14. Detector 130 in FIG. 13 is depicted from the view of the patient's arm. Absorbent layer 131 is in contact with the patient. A plurality of RFID sensors are arrayed on the bottom side of mounting layer 139 of the detector in two circles, an inner group with three sensors 132, and an outer group with three sensors 134. The detector should be placed with the sensors centered on the access site. Mounting layer 139 includes two strips of adhesive 137 on the same side as the sensors 132, 134. The mounting layer also includes an RFID reader 135, mounted on the side of mounting layer 139 away from the sensors. In this embodiment, mounting layer 139 is a little larger than the absorbent material or gauze layer, so that the adhesive strips 137 overlap and may adhere to the patient.

Another embodiment of a detector is depicted in FIG. 14. Detector 140 includes an absorbent layer 141 which is larger and protrudes beyond top mounting layer 149. The detector is adhered to the patient by tape applied by the patient or a care giver. A first group of RFID sensors 142 is arrayed on an inner circle 143 nearer the access site. A second group of RFID sensors 144 is arrayed on an outer circle 146, further away from the access site. RFID reader 145 is mounted on the opposite side of mounting layer 149.

RFID readers are familiar to us as large plastic structures flanking the entrances and exits of retail establishments. These readers are large because they must reliably detect a variety of small RFID tags passing between the readers, whether the tag is near one reader or the other, where the field is stronger, or near the center, where the field is weaker and the RFID tag more difficult to detect. It is clear that such a reader cannot be attached to an RFID detector, with one or more RFID sensors, intended for convenient placement on a patient. Fortunately, a great variety of small RFID readers have been developed and are available commercially.

For example, an RFID reader with a built-in antenna is available from TagSense, Inc., Cambridge, Mass. The reader, a micro-1356 multi-protocol reader is intended for 13.56 MHz systems, and is a little larger than a quarter-dollar coin, about 3 cm square and operates on 5 V. This reader can be programmed and can interface with an external control circuit to send information, an alert signal, an alarm signal, and so on, in case one or more of the RFID tags it monitors does not register and presumptively has detected blood. Similar readers are available for 915 MHz tags, with readers slightly larger, about 4 cm×5 cm. Readers for other RFID frequencies have also been devised. See, e.g., Richard Fletcher et al., *Reconfigurable Agile Tag Reader Technologies for Combined EAS [Electronics Article Surveillance] and RFID Capability*, Proc. Of the Second IEEE Workshop on Automatic Identification Technologies, Summit, N.J. (1999), which is hereby incorporated by reference in its entirety. See also *Low Cost Electromagnetic Tagging: Design and Implementation*, Ph.D. dissertation, Massachusetts Institute of Technology, by Richard Fletcher, September, 2002, which is hereby incorporated by reference in its entirety. Both of these publications teach extremely small RFID readers which can be software-adjusted for frequencies from DC to 300 kHz, from 5-40 MHz, and from 5-15 MHz. Other RFID readers from commercial sources are also available. See, e.g., Model 3020 Series Microreader for 125 kHz tags, from RFID, Inc., Aurora, Colo., U.S.A. This reader is about 5 cm×about 2 cm×about 1 cm thick.

Figure 15:
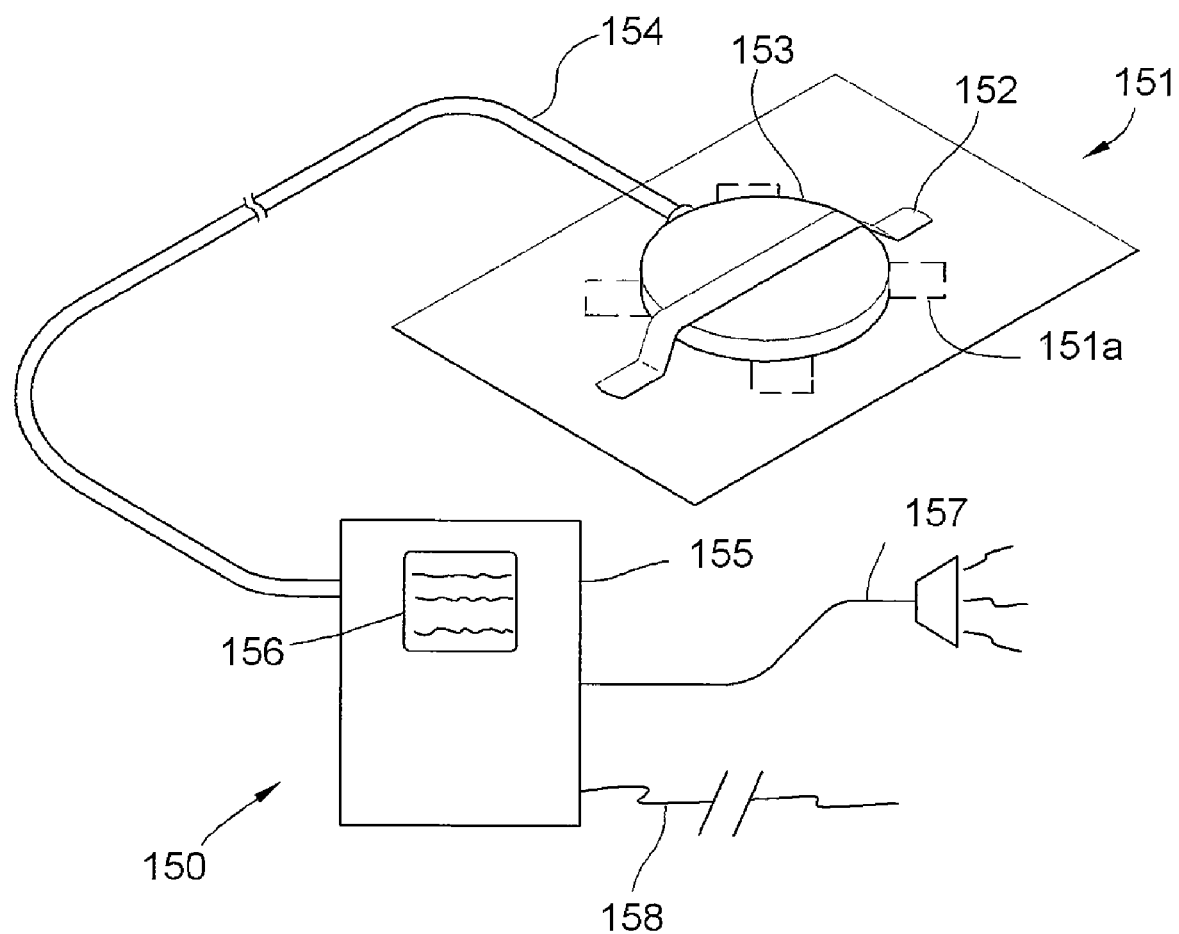
FIGS. 15-16 depict access disconnect detection systems and a hemodialysis machine with an RFID reader and control circuit.

An embodiment of an access disconnect detection system using the above described sensors and readers is depicted in FIG. 15. Access disconnect detection system 150 includes a RFID detector 151 as described above with one or more RFID sensors 151a. An RFID reader 153 is adhered to the top of the RFID detector 151 with a strap 152 which may be integral to a mounting layer of the RFID detector. The RFID reader is connected to the RFID control system 155 via a cable 154. Other ways may be used to attach sensors to a mount or to attach readers to a mount, such as hook and loop fasteners (e.g., those provided by Velcro®), adhesives, and so on.

The RFID control system is mounted nearby, on the hemodialysis machine or other area close to the extracorporeal therapy machine. The RFID control system includes an output device, for example, screen 156 or speaker 157, for locally raising an alert or sounding an alarm. In addition, the RFID control system is connected via a wired connection 158 to a computer/data center in the clinic or hospital for monitoring the hemodialysis or other extracorporeal procedure. In some embodiments, it may be more convenient to place the RFID reader near the patient, rather than at the therapy equipment itself. Thus, the reader may instead be placed on the access needle, near the access needle, elsewhere on the patient, or near the patient.

Figure 16:
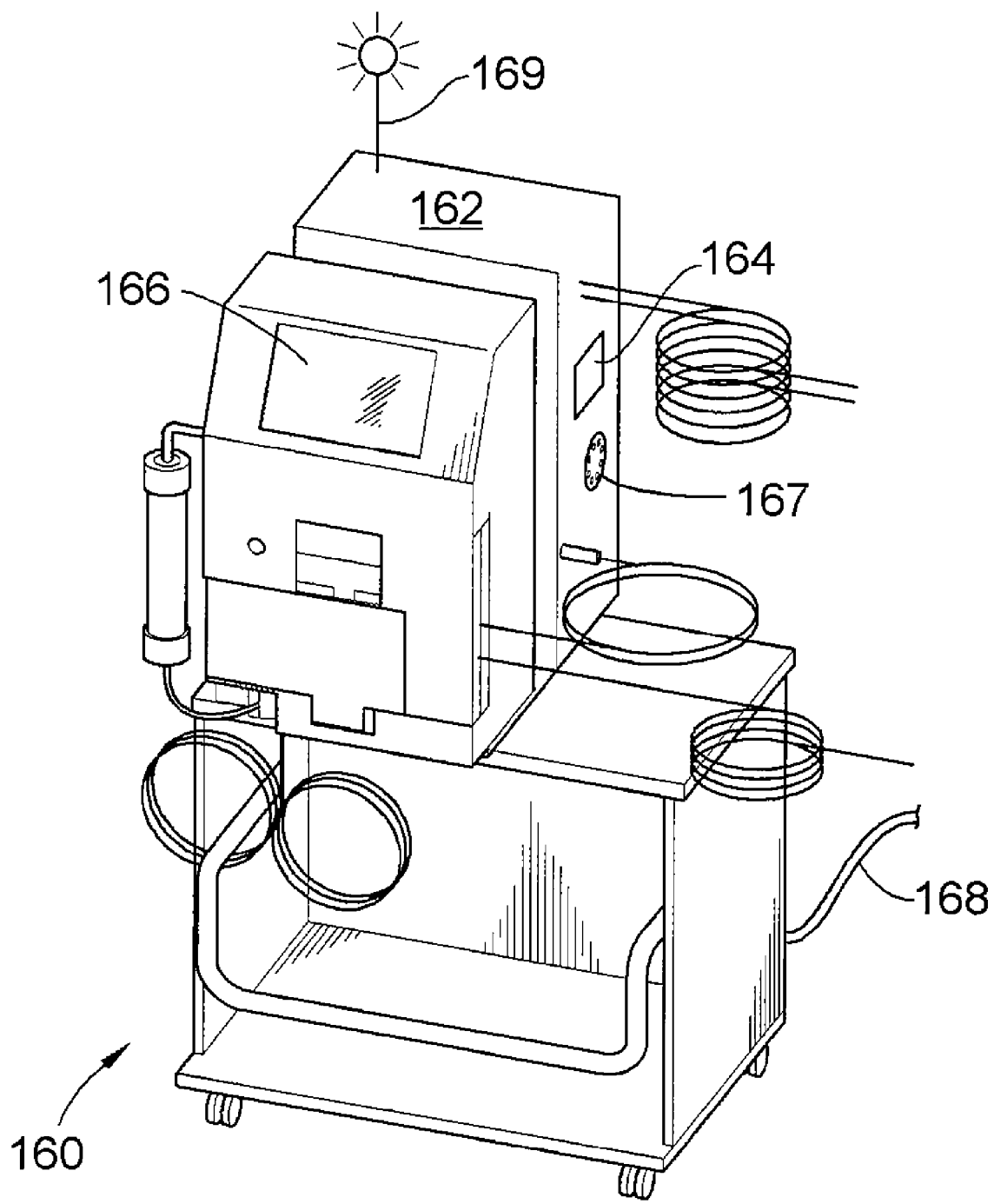

In another embodiment, as depicted in FIG. 16, a hemodialysis machine 160 includes the dialysis machine controller and RFID control circuitry 162 and an RFID reader 164. The hemodialysis machine is also equipped with at least one of a local screen 166 and speaker 167 for local output of an alert or alarm, and is also in communication with a computer or data center in the hospital or clinic wired connection 168 or wireless antenna 169. The hemodialysis machine thus includes controls for the RFID controller, or the RFID controller may be a stand-alone device. Other standards for wireless communication, such as Bluetooth®, may be used instead.

It should be understood that various changes and modifications to the presently preferred embodiments described herein will be apparent to those skilled in the art. For example, it is believed that an absorbent layer placed next to the patient's skin will be of comfort to the patient and will also aid in wicking of blood if any leakage occurs. It is entirely possible that RFID sensor alone, placed on the patient near the access site would suffice. However, the absorbent pad provides tactile and visual comfort to the patient and is virtually necessary for such reasons. Such changes and modifications can be made without departing from the spirit and scope of the present subject matter and without diminishing its intended advantages. It is therefore intended that such changes and modifications be covered by the appended claims.

What is claimed is:

1. An access disconnect detector, comprising:
at least one RFID sensor; and
a mount suitable for mounting the at least one RFID sensor;
wherein the mount and the at least one RFID sensor are configured for positioning adjacent a dialysis access site for detecting a presence of blood of a patient, and wherein the at least one RFID sensor is configured for communication with an RFID reader so that the RFID reader receives one response from the sensor when the sensor is dry and receives a different response or no response when the sensor is wetted with blood.

2. The access disconnect detector according to claim 1, wherein the mount comprises at least one layer of absorbent material and optionally an adhesive layer.

3. The access disconnect detector according to claim 1, wherein the at least one RFID sensor comprises a plurality of RFID sensors mounted in an array.

4. The access disconnect detector according to claim 1, wherein the at least one RFID sensor comprises an RFID inlay.

5. The access disconnect detector according to claim 1, wherein the at least one RFID sensor comprises a thin strip of metal, the strip comprising a plurality of orifices or spaces.

6. The access disconnect detector according to claim 1, wherein the at least one RFID sensor comprises an elongated strip of ductile magnetostrictive ferromagnetic material adjacent a magnetized ferromagnetic strip.

7. The access disconnect detector according to claim 6, wherein at least one of the strips further comprises a plurality of orifices, plurality of spaces, or a serpentine pattern.

8. The access disconnect detector according to claim 1, further comprising a hemodialysis machine with an RFID control circuit and the RFID reader, the RFID control circuit configured for sending a signal and raising an alert if the at least one sensor is not detected.

9. The access disconnect detector according to claim 1, further comprising the RFID reader, an RFID control circuit in operable communication with the RFID reader, and an output device configured for raising an alert if the RFID reader receives the different response or does not detect the at least one RFID sensor.

10. The access disconnect detector according to claim 1, further comprising an RFID reader mounted on the mount or near the at least one RFID sensor.

11. An access disconnect detector, comprising:
a flexible mount suitable for attaching to a patient;
at least one RFID sensor mounted on the mount; and
a pad of absorbent material on an opposite side of the sensors,
wherein the mount and the at least one RFID sensor are configured for positioning adjacent an access site for detecting a presence of blood of the patient, and wherein the at least one RFID sensor and an RFID reader are configured so that the RFID reader receives one response from the at least one sensor when the sensor is dry or wetted with water or perspiration and receives a different response or no response from the least one sensor when the at least one sensor is wetted with blood.

12. The access disconnect detector according to claim 11, wherein the at least one RFID sensor is a printed inlay, each inlay comprising an integrated circuit and an antenna.

13. The access disconnect detector according to claim 11, wherein the at least one RFID sensor comprises an antenna.

14. The access disconnect detector according to claim 11, wherein the RFID sensors comprise dipole antennae or planar spiral antennae.

15. An access disconnect detector, comprising:

a plurality of RFID sensors placed in an array on a mount for mounting the detector to a person; and wherein the mount includes a flexible, porous layer adjacent the RFID sensors, wherein the RFID sensors and the layer are configured for rapid detection of blood from the person.

16. The access disconnect detector according to claim 15, wherein the mount includes a pad for mounting the RFID sensors on an opposite side of the RFID sensors.

17. The access disconnect detector according to claim 15, further comprising a second layer of porous material, the second layer between the RFID sensors and the pad.

18. A method for detecting an access site disconnection, the method comprising:

placing an RFID detector comprising at least one RFID sensor on or adjacent the access site;

attempting to absorb blood leaking from the access site;

detecting the at least one RFID sensor with an RFID reader by pulsing and noting a response from the at least one RFID sensor;

periodically repeating the step of detecting; and sending a signal if the step of detecting receives a different response or no response from the at least one RFID sensor.

19. The method according to claim 18, wherein the at least one RFID sensor comprises a plurality of RFID sensors arrayed adjacent an absorbent layer, and the signal is sent if one or more of the RFID sensors is not detected.

20. The method according to claim 18, further comprising mounting the RFID reader on or adjacent the RFID detector.

21. The method according to claim 18, further comprising raising an alarm with an output device if the at least one RFID sensor sends a different response or no response.

22. The method according to claim 18, further comprising sending the signal after a given number of different or no responses occurs.

* * * * *